(12) United States Patent
Giovanoli et al.

(10) Patent No.: US 9,261,440 B2
(45) Date of Patent: Feb. 16, 2016

(54) PUNCHING DEVICE WITH GRIPPER UNIT

(75) Inventors: Nando Giovanoli, Bivio (CH); Reto Menzi, Filzbach (CH)

(73) Assignee: Hamilton Bonaduz AG, Bonaduz (CH)

( * ) Notice: Subject to any disclaimer, the term of this patent is extended or adjusted under 35 U.S.C. 154(b) by 0 days.

(21) Appl. No.: 14/113,909

(22) PCT Filed: Apr. 29, 2012

(86) PCT No.: PCT/EP2012/057872
§ 371 (c)(1),
(2), (4) Date: Oct. 25, 2013

(87) PCT Pub. No.: WO2012/146770
PCT Pub. Date: Nov. 1, 2012

(65) Prior Publication Data
US 2014/0050637 A1    Feb. 20, 2014

(30) Foreign Application Priority Data

Apr. 29, 2011    (DE) .......................... 10 2011 075 036

(51) Int. Cl.
*G01N 1/08*    (2006.01)
*G01N 1/28*    (2006.01)
(Continued)

(52) U.S. Cl.
CPC ............ *G01N 1/286* (2013.01); *G01N 35/0099* (2013.01); *G01N 1/04* (2013.01); *G01N 1/08* (2013.01); *G01N 2035/00039* (2013.01)

(58) Field of Classification Search
CPC ........... G01N 1/04; G01N 1/286; G01N 1/08; G01N 35/0099; G01N 2035/00039
USPC ...................................................... 73/864.41
See application file for complete search history.

(56) References Cited

U.S. PATENT DOCUMENTS 4,003,151 A * 1/1977 Tolosa et al. .................... 40/575
4,319,271 A * 3/1982 Hurni et al. .................... 348/135
(Continued)

FOREIGN PATENT DOCUMENTS

| CN | 1291283 A | 4/2001 |
|---|---|---|
| CN | 1991330 A | 7/2007 |

(Continued)

OTHER PUBLICATIONS

International Search Report from PCT/EP2012/057872 dated Jul. 16, 2012, 4 pgs.
(Continued)

*Primary Examiner* — Paul Hyun
(74) *Attorney, Agent, or Firm* — Rothwell, Figg, Ernst & Manbeck, P.C.

(57) ABSTRACT

A punching device is provided for processing samples applied to a sample card comprising at least one punching head with a punch and a lower die, the punch being movable between a resting position and a punching position. The punching head has a receiving opening into which a sample card can be introduced by a movable gripping unit, and a punching drive, which drives the movement of the punch between the resting position and the punching position. A piece of sample punched out from the sample card can be discharged at an outlet opening of the lower die into a receiving recess of a receiving container. The gripper unit comprises a sample card gripper and a receiving container gripper which are moveable by a drive unit in three main directions that are orthogonal to one another.

20 Claims, 7 Drawing Sheets

(51) Int. Cl.
*G01N 35/00* (2006.01)
*G01N 1/04* (2006.01)

(56) References Cited

U.S. PATENT DOCUMENTS

| | | | |
|---|---|---|---|
| 5,460,057 | A | 10/1995 | Ostrup |
| 5,641,682 | A | 6/1997 | Pagels et al. |
| 6,699,710 | B1 | 3/2004 | Kononen et al. |
| 2005/0223837 | A1* | 10/2005 | van der Meulen ......... 74/490.01 |
| 2007/0059205 | A1 | 3/2007 | Ganz et al. |
| 2008/0063562 | A1 | 3/2008 | Hoover et al. |
| 2010/0105035 | A1* | 4/2010 | Hashsham et al. ................ 435/6 |
| 2011/0034343 | A1 | 2/2011 | Erling et al. |
| 2011/0132111 | A1* | 6/2011 | Shoemaker et al. ....... 73/864.41 |

FOREIGN PATENT DOCUMENTS

| | | |
|---|---|---|
| DE | 693 08 957 T2 | 9/1997 |
| DE | 600 28 352 T2 | 3/2007 |
| EP | 0753747 A2 | 1/1997 |
| EP | 1804047 A2 | 7/2007 |
| WO | 2005093434 A1 | 10/2005 |
| WO | 2010/001023 A2 | 1/2010 |
| WO | 2010/009173 A1 | 1/2010 |
| WO | 2011/067309 A1 | 6/2011 |

OTHER PUBLICATIONS

German Search Report from 10 2011 075 036.3 dated Apr. 13, 2012, 8 pgs.
Office Action with English translation issued in copending Chinese Patent Application No. 2012800206963, 13 pages (Dec. 23, 2014).
Search Report issued in copending Chinese Patent Application No. 2012800206963, 2 pages (Dec. 5, 2014).
Notice of Reasons for Rejection issued in copending Japanese Patent Application No. 2014-506904, 13 pages (Oct. 6, 2014).

* cited by examiner

PUNCHING DEVICE WITH GRIPPER UNIT

CROSS REFERENCE TO RELATED APPLICATION

This application is a 35 U.S.C. 371 National Phase Entry Application from PCT/EP2012/057872 filed Apr. 29, 2012, which claims the benefit of German Patent Application No. 10 2011 075 036.3 filed on Apr. 29, 2011, the disclosure of which is incorporated herein in its entirety by reference.

The present invention relates to a punching device for processing dried samples applied to a sample card, in particular of liquids containing DNA such as blood, saliva and the like.

In such punching devices, a plurality of sample cards are kept in a magazine for sample cards and are removed from the magazine in a particular order by means of a gripper unit and fed to a punching means of the punching device. In an area, previously captured by means of imaging methods, in which the applied sample has been identified on the sample card, at least one sample piece is then punched out of the sample card. It is also possible for a plurality of sample pieces to be punched simultaneously or in succession out of the same sample area. The punched out sample pieces are guided through an outlet opening in a lower die by the movement of a punching pin (punch) and in this way transported into a receiving recess in a receiving container, preferably into a well of a microtiter plate. As soon as sample pieces have been punched out of all the desired sample cards and have been received in the receiving container, the analysis of the individual samples contained in the sample pieces can take place by means of methods such as PCR for DNA analyses, high-performance gas chromatography (HPLC) or the like, wherein, for this purpose, further steps, which are not described in detail in the scope of the present application, are carried out after punching out.

A method and a device for automatically punching sample pieces out of sample cards is known for example from U.S. Pat. No. 5,641,682.

Furthermore, a punching device of the abovementioned type is known under the designation "BSD1000-GenePunch" from BSD Robotics (a Luminex Company, in Brisbane, Queensland 4110, Australia). An associated product flyer was available at the following Internet address at the time that the present application was filed: http://www.bsdrobotics.com/Documents/Brochure/BSDR1000(10)%20-%20BSD1000%20GenePunch.PDF.

Furthermore, the mode of operation of this punching device is disclosed in a video film which was available at the following Internet address at the time the application was filed: http://www.bsdrobotics.com/Videos/BSD1000.wmv.

The following mode of operation can be seen from the video film: In the "BSD1000-GenePunch" punching device, a gripper device for sample cards is moved from a magazine, from which the gripper device has removed a sample card, along a horizontally extending rail to a scanner into which the sample card is introduced and subsequently scanned. The gripper device is in this case movable in two directions which are orthogonal to one another, specifically along the rail and orthogonally to the latter, such that the grasped sample card is movable in two dimensions in its card plane. After scanning, the sample card is transported by means of the gripper device to the punching means of the punching device and positioned relative to said punching means, in order that a sample piece can be punched out at that position of the sample card that is evaluated after scanning. The punched-out sample piece is subsequently dispensed into a receiving container, for instance a well of a microtiter plate, arranged under the punching means. In the case of this punching device, a plurality of receiving containers are arranged in a star shape around a rotation axis orthogonal to a horizontal plane, and the position thereof, in particular of a particular well, relative to the punching means takes place by means of a rotary movement and by means of displacement in the horizontal plane. After the punching of one or more sample pieces out of a sample card has been completed, the gripper device transports the punched sample card back along the rail to the card magazine and sets it down there again. The gripper device is then briefly pulled back until the card magazine has been moved upward by one position in order to be able to remove the next sample card from the magazine.

In general terms, a punching device known from the prior art thus comprises at least one punching means having a punch and a lower die, wherein the punch is movable between a rest position in which it is away from the lower die and a punching position in which it is close to the lower die, and wherein the punching means has a receiving opening into which a sample card from a sample card container is introducible by means of a movable gripper unit of the punching device and is positionable relative to the punching means, and a punching drive which is couplable or coupled to the punch of the punching means and by way of which the movement of the punch between the rest position and the punching position is driven, wherein the punching means is set up such that a sample piece punched out of the sample card can be dispensed at an outlet opening of the lower die into a receiving recess in a receiving container arranged beneath the punching means.

In the known punching device, the sample cards are grasped by a gripper means and transported to the punching means. The gripper means is movable only in one plane, and so different sample cards can be removed only by moving the magazine with sample cards. Automated grasping and transporting of receiving containers is not possible, since the receiving containers have to be inserted manually into the receiving frame arranged in a star shape.

It is therefore the object of the invention to develop a punching device of the abovementioned type such that optimized handling of sample cards and receiving containers is enabled.

In order to achieve this object, it is proposed that the gripper unit comprises a sample card card gripper means and a receiving container gripper means which are movable jointly by means of a drive unit in three main directions that are orthogonal to one another. Such a configuration makes it possible to use a drive unit, preferably having a plurality of drives, which are set up for transport in the different main directions, for two different gripper means. This produces advantages in the handling of the gripper unit due to the drive unit to be actuated in an identical manner, this representing a simplification for operation and programming. As a result of the use of the common drive unit, it is possible to save costs both in production and in maintenance.

It is proposed that the sample card gripper means and the receiving container gripper means each have a gripper drive, by means of which associated grippers of the sample card gripper means and of the receiving container gripper means are movable, in particular pivotable, between an open position and a closed position. By way of the individual gripper drives, these can be optimized and set up optimally for the respective gripping task, in order to meet the various requirements which are set for the grasping/transporting of relatively thin, smooth sample cards from a magazine or for the grasping/transporting of receiving containers which may also be filled with liquid.

In this case, it is preferred for the sample card gripper means, in particular the associated grippers thereof, to be pivotable about a pivot axis by means of the associated gripper drive, such that it is pivotable between a loading/unloading position facing the sample card container and a waiting position facing away from the sample card container.

To this end, it is proposed in a development that the sample card gripper means is furthermore pivotable into a punching position located between the loading/unloading position and the waiting position, in which punching position a sample card grasped by the associated grippers is able to be fed to the punching means.

The pivoting of the grippers of the sample card gripper means can take place in an angular range of about 180° between the loading/unloading position as the starting point (0°), in which the grippers are oriented substantially vertically downward, and the waiting position as the end point (180°), in which the grippers are oriented substantially vertically upward. The punching position, located in between, is at about 90°, such that the grippers are oriented substantially horizontally. In particular the waiting position does not necessarily have to be at 180°, and the angle can be somewhat smaller or larger.

The sample card gripper means and the receiving container gripper means are preferably actuated by a control unit of the punching device such that when a receiving container is grasped and transported by means of the receiving container gripper means the sample card gripper means has been pivoted into its waiting position. At the waiting position, it is essential that the grippers of the sample card gripper means can be moved into a position in which they do not restrict the movement of the gripper unit, this being important in particular for the grasping and transporting of receiving containers by means of the receiving container gripper means.

In a development, it is proposed that the punching device has a receiving plate supporting the receiving container and having a light source illuminating at least a part of a receiving plate, wherein the light source is arranged such that at least a part of a receiving container located on the receiving plate, in particular receiving recesses provided in said receiving container, can be illuminated from the direction of the receiving plate, in particular from below.

In this case, it is preferred for at least one electroluminescent film to be provided as light source on the receiving plate, wherein preferably the receiving plate is a transparent plate, preferably a glass plate, and wherein the EL film is arranged preferably on the underside of the receiving plate.

The punching device may furthermore have a transport frame which rests on the receiving plate, is movable in the plate plane and in which at least one receiving container is receivable.

The receiving plate preferably forms a cover of a housing for a drive unit which allows the transport frame to move on the receiving plate, wherein preferably the transport frame is coupled in a contactless manner by means of magnets to the drive unit covered by the receiving plate.

The punching device is preferably set up such that receiving containers are transportable by means of the gripper unit from waiting positions outside the receiving plate to processing positions on the receiving plate and vice versa.

It is furthermore proposed that the gripper unit is configured such that receiving containers can be moved toward and away from the transport frame by means of the gripper unit, wherein a receiving container in question is held by means of the receiving container gripper means during transport.

The punching device may be combined with a metering device, wherein the gripper unit is fitted on a support which is movable in one of the main directions and on which a pipetting device, which is movable in the two other main directions, of the metering device is additionally fitted, such that the gripper unit and the pipetting device are moved simultaneously in the one main direction.

The invention is described in the following by way of example and in a nonlimiting manner with reference to the appended figures.

Figure 1:
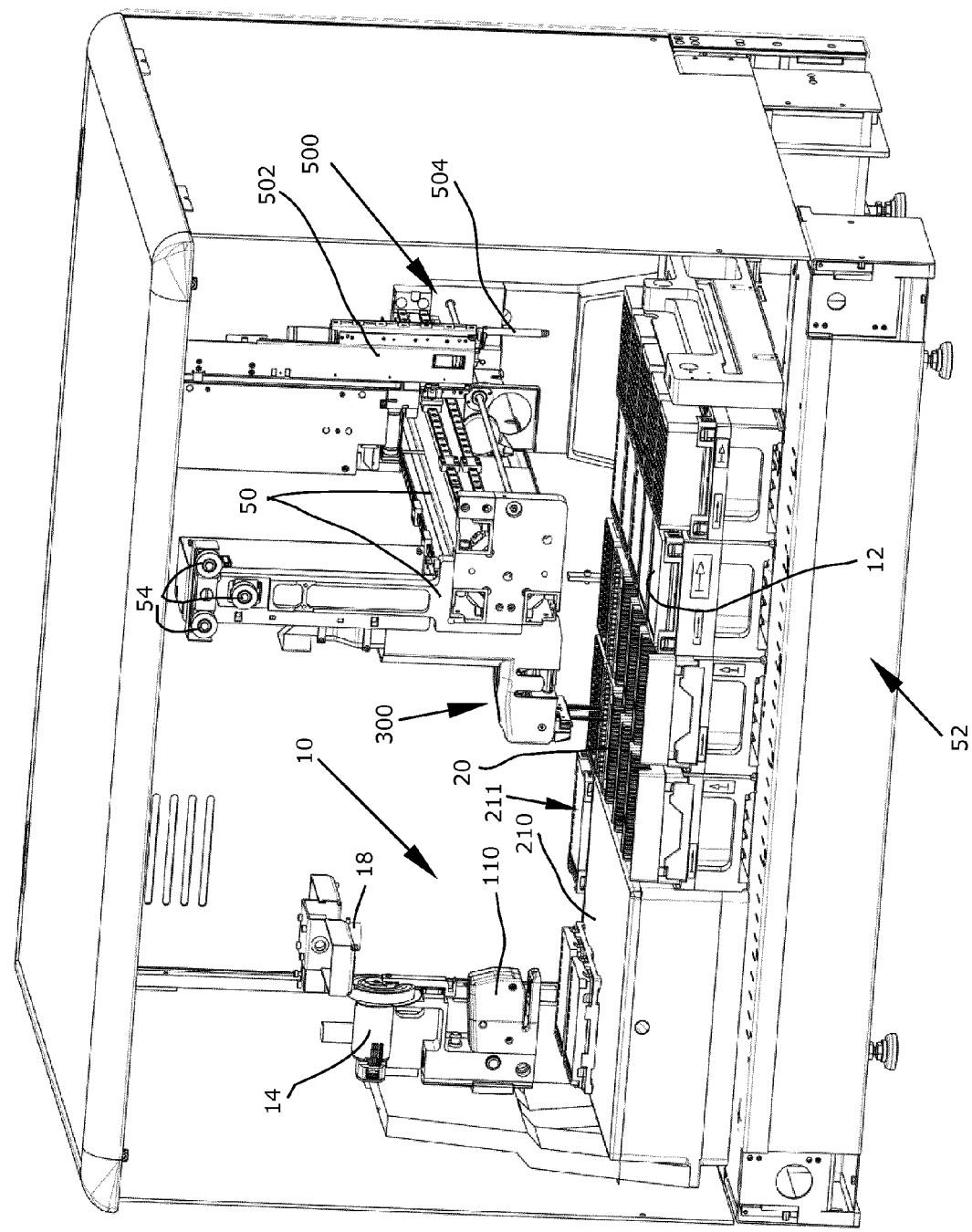
FIG. 1 shows a schematic perspective illustration of a punching device in combination with a metering device.

FIG. 1 shows an overall view of a punching device 10, which is optionally combined here with a metering device 500. In the combination illustrated here, the punching device 10 and the metering device 500 use a common support 50 which is movable in one of the main directions X, Y, Z, namely in the longitudinal direction X. To this end, the support 50 is mounted by means of rollers 54 on longitudinal rails (not illustrated), in the upper region of a support structure 52 which is provided for the overall device but only illustrated in part here. Of course, a drive device (not illustrated) for the support 50 is also present, said drive device being actuable via a control unit (likewise not illustrated) of the overall device.

The metering device comprises a pipetting device 502, fitted on the support 50 so as to be movable in the two other main directions Y, Z, that is to say the transverse direction Y and the vertical direction Z, having at least one pipetting channel 504 for drawing and dispensing liquid into/out of provided receiving containers 12 or a reservoir for the liquid to be metered. The metering device 500 is configured as an automated pipetter, known per se, and will not be described in further detail here.

Fitted on that side of the support 50 that is opposite the pipetting device 502 is a gripper unit 300 which is likewise configured to be movable in the two other main directions Y, Z.

This gripper unit 300 should be considered, in the scope of this application, as belonging to the punching device 10, even if in the present example it is fitted on a support 50 that is used jointly with the pipetting device 502. Furthermore, the punching device 10 comprises, as further main components, a punching drive 14, a punching means 110, an image recording device 18 and a receiving plate 210. Furthermore, magazines 20 for in each case a plurality of sample cards 22 (FIG. 3) can be seen in FIG. 1. By means of the gripper unit 300, a sample card is removed from a magazine 20 and fed to the punching means 110, so that by means of the punching means 110 at least one sample piece can be punched out of the respective sample card.

The function of the modular punching means 110, which, due to its self-contained structure, can be easily separated from the punching device 10, is described only in part in the scope of this application. For details concerning the configuration of the modular punching means (punching head) 110, reference is made to the application, filed simultaneously by the applicant, having the title "Punching device having a modular punching means" (application number DE102011075035.5), the content of which is incorporated here by reference with respect to the configuration of the punching means.

Likewise, in the scope of this application, special features of the receiving plate 210 are only dealt with in part. For details concerning the configuration of this receiving plate or of a drive (not visible in FIG. 1), covered by the receiving plate 210, for positioning receiving containers relative to the punching means 110, reference is made to the two simultaneously filed applications with the title "Punching device with receiving plate" (application number DE102011075037.1) and "Punching device with illuminated receiving plate" (application number DE102011075039.8), the content of both of which is incorporated here by reference with respect to the configuration of the receiving plate and the drive covered by the latter.

Figure 2:
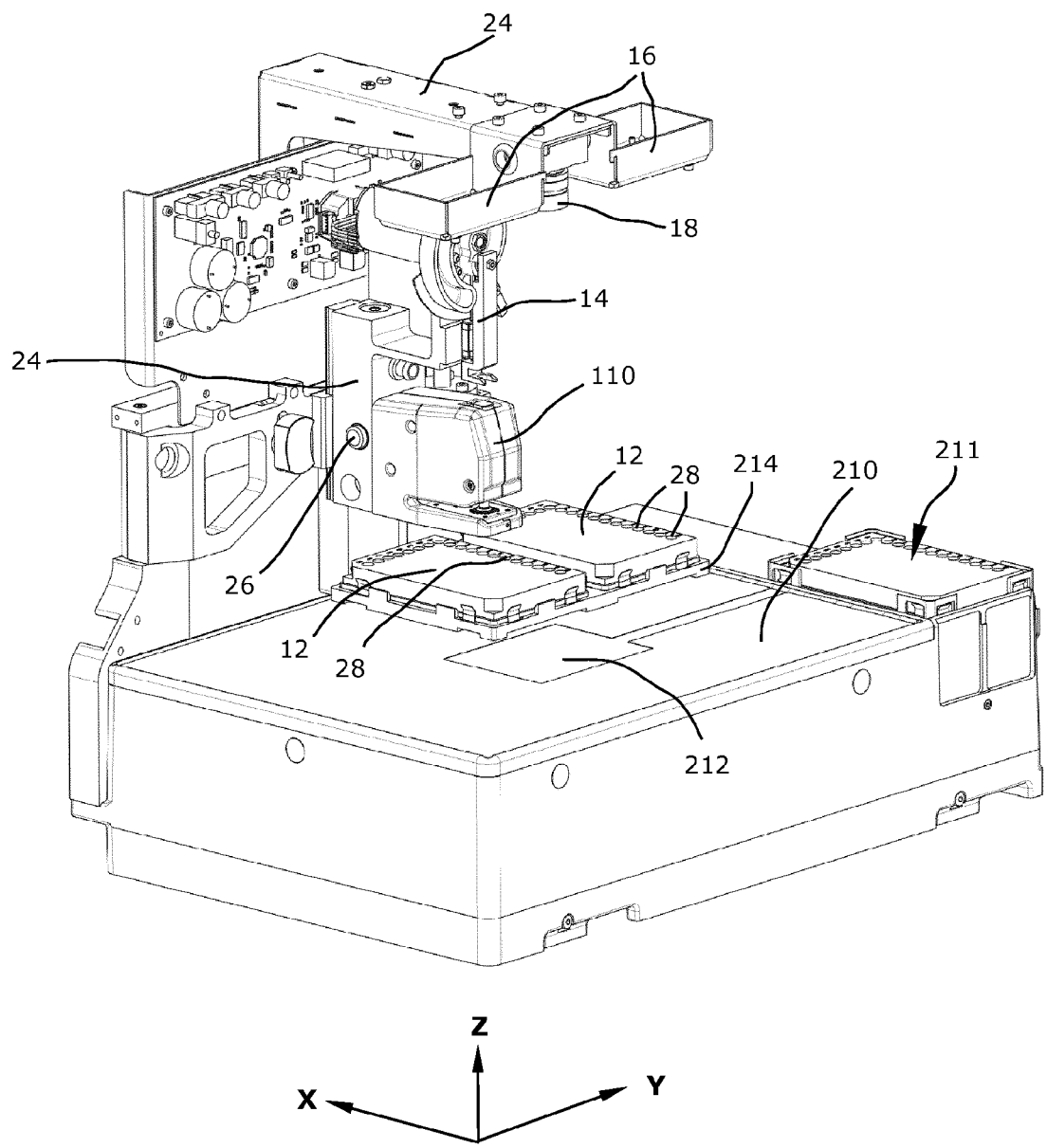
FIG. 2 shows a schematic perspective illustration of the punching device without a metering device and without a gripper unit.

FIG. 2 shows a schematic perspective illustration of the punching device 10 without a gripper unit 300. The punching device 10 comprises a frame-like structure or support structure 24, to which the punching drive 14 and the image recording device 18 are fastened, and on which the punching means 110 is fitted in a removable manner as a punching means module. FIG. 2 shows the state in which the modular punching means 110 is coupled to the structure 24 of the punching device. In order to be able to remove the punching means 110 from the structure 24, it is proposed that an actuating element or push button 26 can be actuated so that an engagement between the punching means 110 and the support structure 24 can be released. The receiving plate 210 serves for mounting or supporting at least one receiving container 12, which is preferably provided as a microtiter plate having a particular number of wells (receiving recesses) 28. It is also possible for different microtiter plates to be used, and the number of wells 28 is not limited per se, except with regard to the fact that a sample piece punched out of a sample card has space in a corresponding well 28.

It is also apparent from the overview illustration in FIG. 2 that the image recording device 18 is arranged substantially vertically above an illuminated area 212 of the receiving plate 210. This illuminated area 212 is formed preferably by an electroluminescent film received in the receiving plate or arranged on the rear side thereof. A microtiter plate 12 arranged thereon can be backlit by the EL film 212, such that an image of the backlit microtiter plate 12 or of a part thereof can be captured by the image recording device 18. The microtiter plate(s) 12 is/are received on the receiving plate 210 in a transport frame 214 which is coupled via magnets (not illustrated here) to a drive unit located under the receiving plate 210 and can be moved on the receiving plate 210 relative to the stationary punching means 110 by means of this drive unit. As a result, a particular receiving recess 28 of a receiving container 12 can be arranged precisely beneath the punching means 110, such that a punched-out sample piece drops into this receiving recess or is received in the latter. Provided on both sides of the image recording device 18 are holders 16 for alternative illumination means, which illuminate from above an article, preferably a sample card, positioned under the image recording means 18, so that image-processing processes can be carried out for the sample card, for example recognition of a bar code or the like.

Figure 3A:
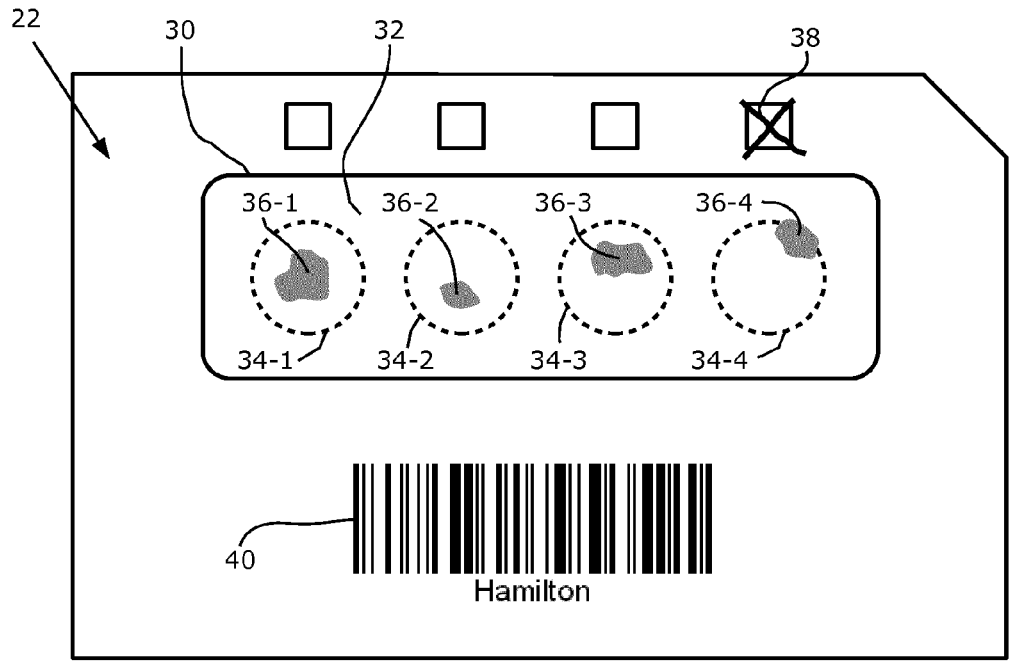
FIG. 3 shows, in partial figures a) and b), schematically illustrated sample cards in the state prior to the punching out of sample pieces (FIG. 3a) and after the punching out (FIG. 3b).
Figure 3B:
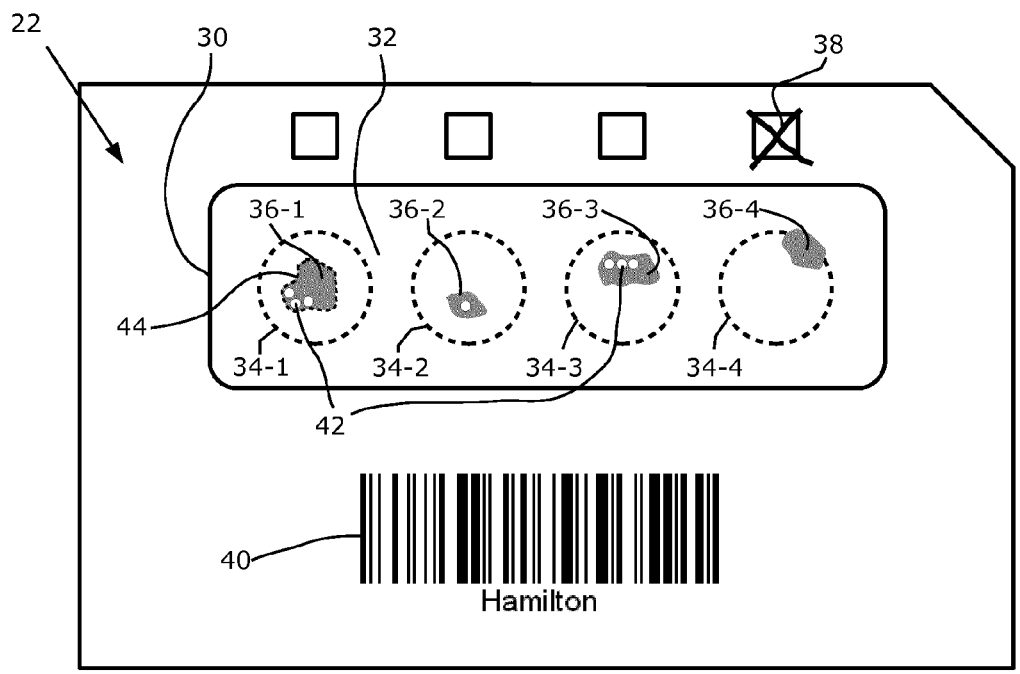

FIG. 3 shows, in partial figures a) and b), an example of a sample card 22. The sample card has a kind of opening 30, in which an absorbent material 32, for instance a kind of filter paper or the like is visible. At least one sample area is identified on the absorbent material, and in the present case there are four such sample areas 34-1 to 34-4, which are illustrated as dashed circles. If samples, such as blood, saliva or other liquids are collected by means of the sample card 22, the liquid samples are intended to be deposited as far as possible within the marked sample areas 34-1 to 34-4. In the present example, samples 36-1 to 36-4 of different sizes, for example drops of blood or samples of saliva, have been deposited in the corresponding sample areas 34-1 to 34-4. The sample 36-4 is in this case not located completely within the marking of sample area 34-4, and so this sample has correspondingly been indicated as invalid by a sample donor or by a member of medical staff by way of a cross 38 above the sample area 34-4. A code (bar code, 2D bar code or the like) 40 is also provided on the card beneath the absorbent material 32, in order to allow the sample card to be identified and to be assigned to a sample donor, a collecting institute or the like. Further information, such as manufacturer's information, information regarding the purpose of the card or regarding the sample liquid, etc. may also be contained or printed on the sample card 22. The samples 36-1 to 36-4 applied in liquid form are absorbed by the absorbent material 32 and subsequently dry. After drying, sample pieces can be punched out of the samples 36-1 to 36-4 by means of the punching means 110. After a plurality of sample pieces have been punched out of the samples 36-1 to 36-3, the sample card 22 is indicated in FIG. 3b by the white punched holes 42. Where and in what order sample pieces were punched out can be established for example by means of image processing, wherein it is firstly possible to detect whether a sample is located within the marked sample area 34-1 to 34-4 (for example by using the cross 38), where the sample 36-1 to 36-4 is located within the sample area 34-1 to 34-4, and what boundary it has, this being indicated by the dashed line 44 in the case of the sample 36-1. Using such information and the desired number of sample pieces to be punched out, it is possible to identify where sample pieces should be punched out. Accordingly, the sample card 22 can then be positioned relative to the punching means so that the sample pieces can be punched out at the predetermined points. The form illustrated here of the sample card is purely by way of example, and the sample card can have some other format, more or fewer, smaller or larger sample areas 34, etc.

Figure 4:
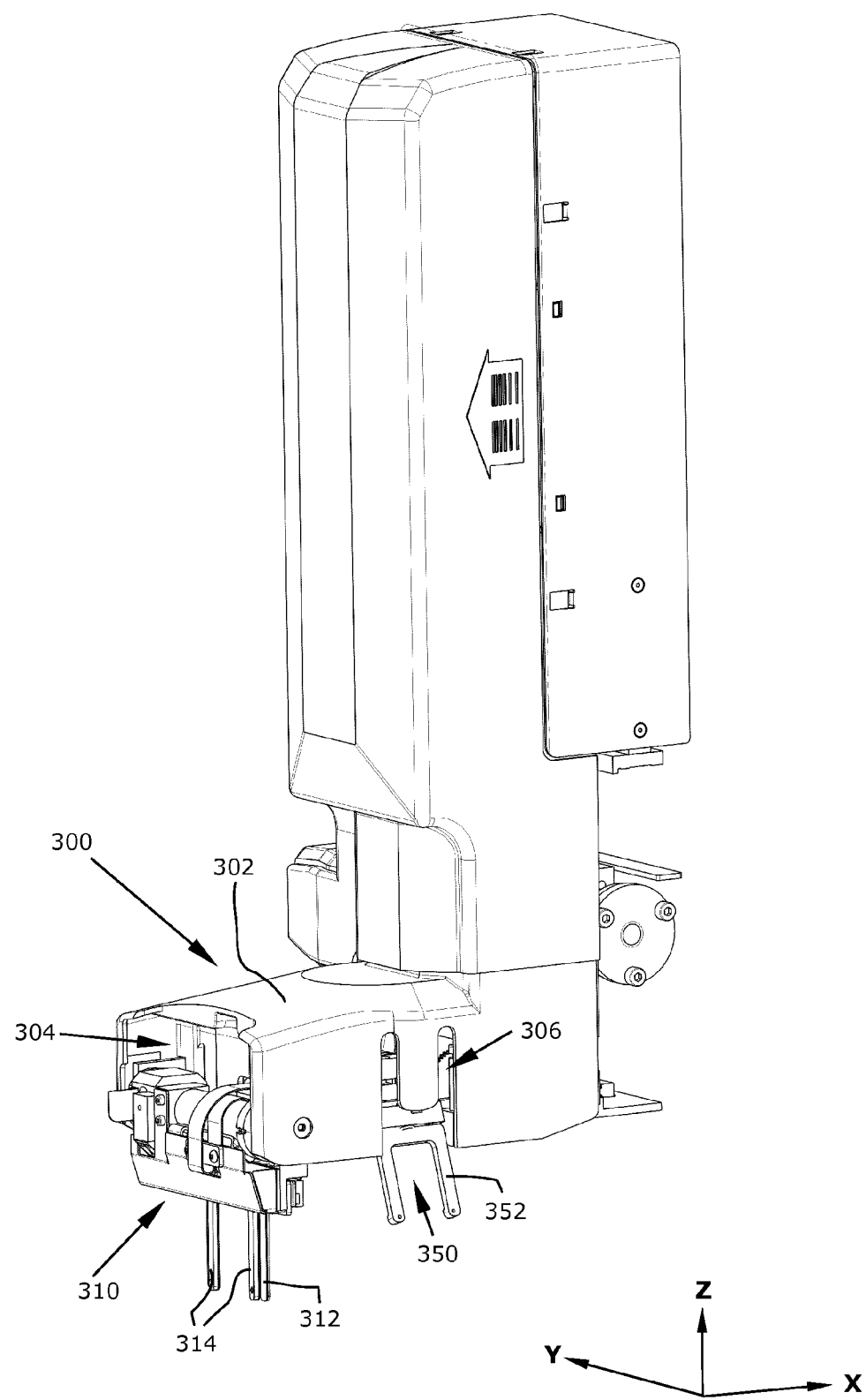
FIG. 4 shows an enlarged schematic perspective illustration of a gripper unit from FIG. 1.

FIG. 4 shows an enlarged illustration of the gripper unit 300. It is movable as a whole in all three main directions X, Y, Z relative to the punching means 110 (FIG. 1). In this case, the movement in the X direction takes place by the support 50 being moved, and the movement in the Y and Z directions takes place by way of a relative movement of the gripper unit 300 with respect to the support 50 by means of corresponding drives (not visible). These drives form, together with the drive of the support 50, the drive unit for the movement of the gripper unit 300 in the three main directions X, Y and Z.

In order to remove sample cards from a magazine, the gripper unit 300 has a sample card gripper means 310 having card grippers 312 and 314. The card grippers 312, 314 are movable relative to one another such that they can be moved, in particular pivoted, away from one another in order to form an acute angle in between as an opening for introducing a sample card. Once the sample card has been received between the card grippers 312, 314, they can be moved toward one another again so that the sample card is clamped between them and thus held. Furthermore, the gripper unit comprises a receiving container gripper means 350, of which only one container gripper 352 is visible. A further container gripper 354 (FIG. 5) is located, with respect to the illustration in FIG. 4, on a rear side, which cannot be seen, of the gripper unit 300. In order to protect the gripper unit 300 or in order to protect its respective gripper means 310, 350 and the gripper drives thereof, described below, a gripper housing 302 is provided. The gripper housing 302 has openings 304 and 306 which are formed such that the desired movements of the respective grippers 312, 314, 352, 354 are not hindered.

The mode of operation of the two gripper means 310 and 350 will now be described with reference to FIGS. 5 to 10, which show simplified perspective illustrations and associated sectional illustrations, in which particular operating states of the gripper means 310 and 350 are visible.

The two gripper means 310 and 350 are fitted on a common frame structure 330, which in turn is itself fitted on a connection piece (not explained in more detail) of the drive unit for the gripper unit 300, wherein this connection piece is connected to the support 50 and is movable in the Y and Z directions relative to the latter, together with the gripper unit 300 fastened thereto.

Figure 5:
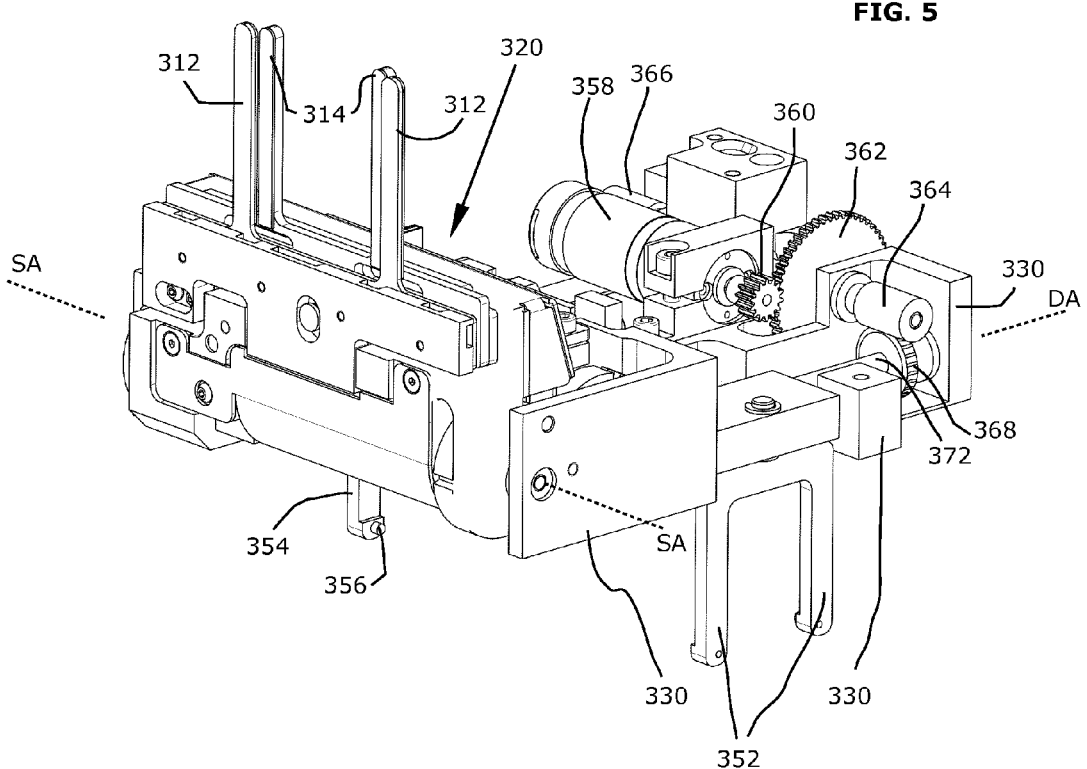
FIG. 5 shows a perspective schematic illustration of a sample card gripper means and of a receiving container gripper means.

The card grippers 312, 314 can be pivoted jointly about a pivot axis SA by means of a card gripper drive 320. In FIG. 5, the card grippers 312, 314 are in a waiting position in which they are oriented substantially vertically upward. In this waiting position, the card grippers 312, 314 do not limit the movement of the gripper unit 300 in any of the main directions X, Y, Z, and so a receiving container 12 (FIGS. 1 and 2) can be grasped and transported for example by means of the container grippers 352, 354. In order to remove a sample card from a magazine 20 (FIG. 1) arranged beneath the gripper unit 300, the card grippers 312, 314 can be pivoted into their loading/unloading position according to FIG. 6, in which they are oriented substantially vertically downward. In this position, the card grippers 312, 314 can be moved downwardly in the Z direction in the direction of a sample card by the entire gripper unit 300 being moved, and, after grasping said sample card, can remove it from the magazine upwardly in the Z direction. During this operation of receiving or returning a sample card from or into a magazine, the container grippers 352, 354 are pivoted preferably into their waiting position illustrated in FIG. 6, so that they cannot hinder the downward movement of the gripper unit toward the sample card or magazine.

Figure 7:
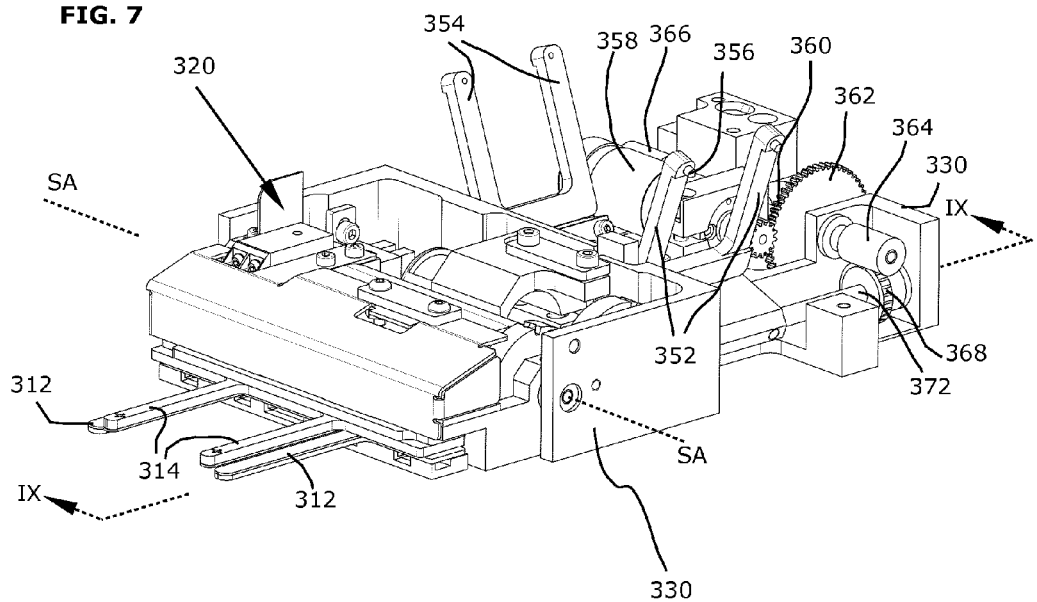
FIG. 7 shows a perspective schematic illustration of the sample card gripper means and of the receiving container gripper means in another position.

A sample card grasped by the card grippers 312, 314 can, after being withdrawn from the magazine, be pivoted about the pivot axis SA together with the card grippers 312, 314 holding it, preferably into the punching position according to FIG. 7, in which the card grippers 312, 314 and a sample card (not illustrated) optionally held thereby are oriented substantially horizontal. In this substantially horizontal position, the sample card can be transported by means of the gripper unit in the direction of the punching means 110 and be introduced there into the receiving opening thereof. As a result of the movement of the gripper unit in particular in the X and Y directions, the sample card can be oriented exactly relative to the punching means, in particular to the punch thereof, so that a sample piece can be punched out at a predetermined point of the sample card. Prior to punching out, a sample card held by the card grippers 312, 314 can also be arranged beneath the image capturing device 18 (FIGS. 1 and 2), by means of which an image of the sample card is recorded, it being possible subsequently to evaluate said image in order for example to detect an identification code 40 (FIG. 3) or samples 36-1 to 36-4 and to calculate therefrom the position of the sample card relative to the punching means 110. In order also to be able to determine the relative position of the sample card with respect to the gripper unit 300 or to the card grippers 312, 314, the card grippers 314 have on their top side positioning crosses 316 which are readily detectable by means of image processing. During the image recording of the sample card for the purpose of analyzing elements visible thereon, such as coding 40, a cross 38 (FIG. 3), samples 36-1 to 36-4, the card can be illuminated from above by means of illumination means, for instance LEDs and the like, present on the holders 16 (FIG. 2), in order to ensure optimal illumination and to be able to carry out image recognition optimally.

After at least one sample piece has been punched out of the sample card, it is possible for the sample card to be held over the electroluminescent film 212 of the receiving plate 210 for the purpose of checking, and for a further image of the sample card to be captured by means of the image capturing device, the punched-out hole, backlit by the EL film 212, in the sample card being readily detectable in said image. If for example an EL film 212 having a particular color, for instance blue, green or red, is used, punched-out regions in the sample card, through which regions the colored, in particular blue, green or red light, passes through, represent the only points in an image that appear in such a color (blue, green, red). However, detecting punched-out regions is conceivable not only immediately after punching out, but can also take place prior to a (further) punching operation, in order to check whether the card in question has already been punched and from which of the samples 36-1 to 36-4 one or more sample pieces have been removed.

As soon as the process for one sample card has been finished, the latter can be transported back to its previous position in the magazine. Alternatively, it is conceivable to deposit it in a different magazine in which only previously processed sample cards are contained. Subsequently, a new sample card can be removed from the magazine and fed to the punching process.

Figure 6:
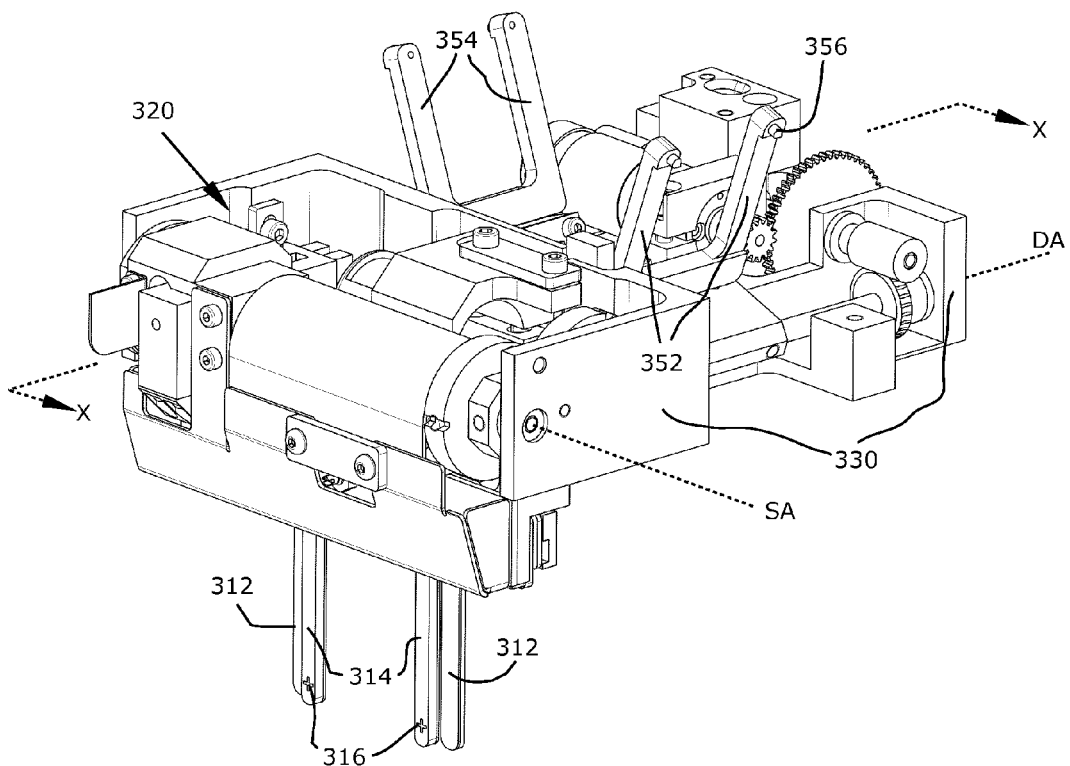
FIG. 6 shows a perspective schematic illustration of the sample card gripper means and of the receiving container gripper means in another position.

The container grippers 352, 354 are illustrated in FIG. 5 in their gripping position, in which they are oriented substantially vertically downward, and hold a receiving container 12 (FIGS. 1 and 2) in a clamped manner between one another. In order to allow optimal coupling between the receiving container 12 and the grippers 352, 354, the grippers have, on their sides facing the receiving container, engagement pins 356 which can engage in corresponding engagement holes in the receiving container. The two container grippers 352, 254 are pivotable about respective mutually parallel rotation axes DA so that they can be pivoted from their gripping position (FIG. 5) into a waiting position in which they are directed obliquely upward (FIG. 6). The pivoting movement of the two container grippers 352 and 354 takes place synchronously by means of a motor 358 (electric motor), the pinion 360 of which meshes with a gear wheel 362. The gear wheel 362 has worm gears 364 and 366 on both sides of its rotation axis, said worm gears being in engagement with gear wheels 368 and 370 which are fitted on rods 372, 374 to which the container grippers 352, 354 are fastened for conjoint rotation. This drive mechanism for the container grippers 352, 354 is also visible in the two sectional illustrations in FIGS. 9 and 10.

A receiving container grasped by the container grippers 352, 354 can be set down at any desired position by means of the gripper unit 300 in order to be used subsequently during punching or during filling with liquid by means of the pipetting device 502. In this case, the gripper unit is also used, in order, with reference to FIGS. 1 and 2, to transport a sample container 12 from a position between sample card magazines 20 (left-hand side) and pipette tip containers (right-hand side) to a position 211 next to the receiving plate 210 or to a position on the transport frame 214 on the receiving plate 210. In order for example to allow a receiving container 12 to be transferred into the transport frame 214, the transport frame 214 can be moved, with reference to FIG. 2, into a position on the receiving plate 210 in which it is not covered upwardly by an element of the punching device 10, for instance punching means 110, image capturing device 18 or the like, so that the gripper unit can be positioned without hindrance above the transport frame 214 in order to set down or pick up a receiving container.

Figure 8:
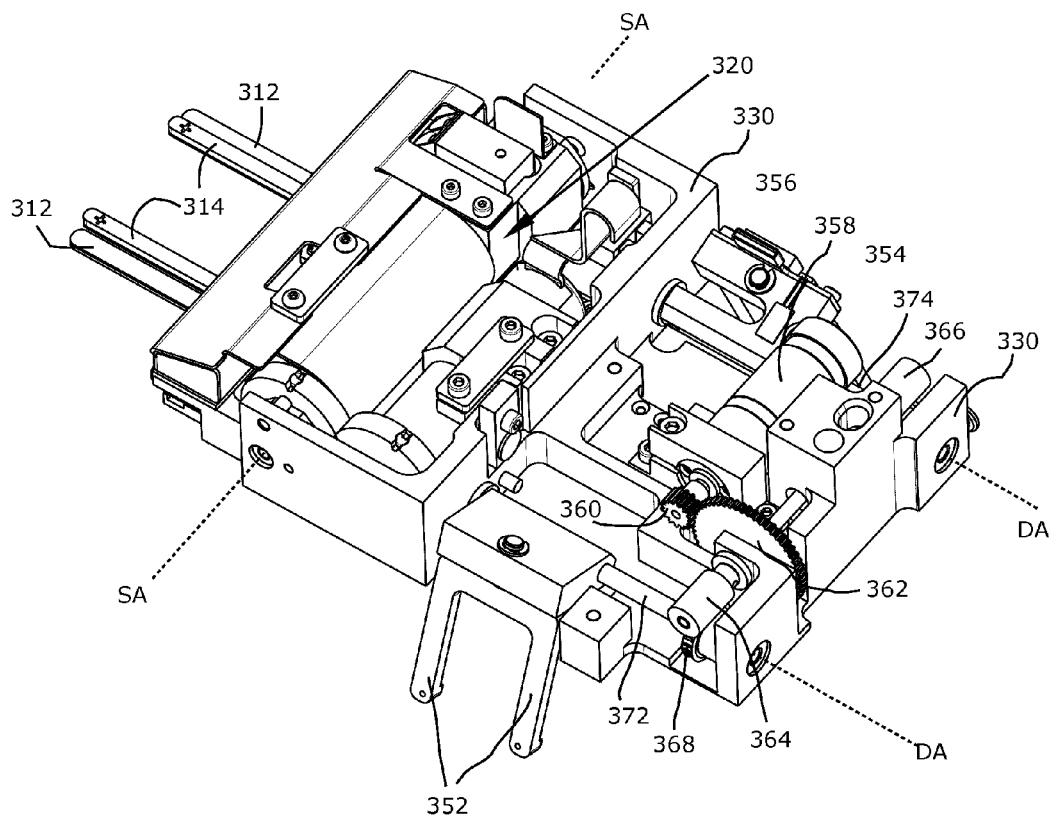
FIG. 8 shows another perspective illustration of the sample card gripper means and of the receiving container gripper means.
Figure 9:
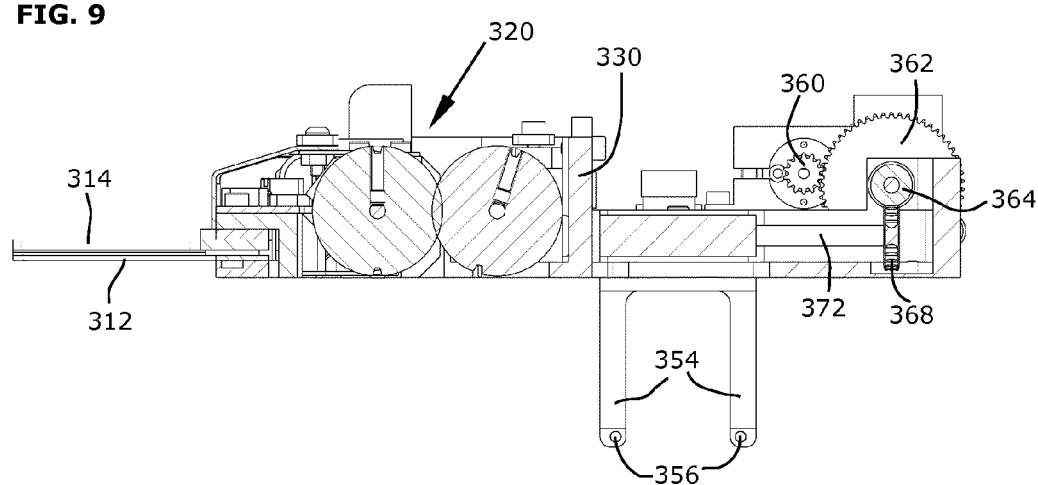
FIG. 9 is a sectional view corresponding to the section line IX-IX in FIG. 7.

In FIG. 8, the card grippers 312, 314 are illustrated in the punching position (similarly to FIGS. 7 and 9) and the container grippers 352, 354 are illustrated in a standby position immediately before grasping or after setting down a receiving container. In this illustration, the positioning crosses 316 on the top side of the card gripper 314 are also readily visible.

Figure 10:
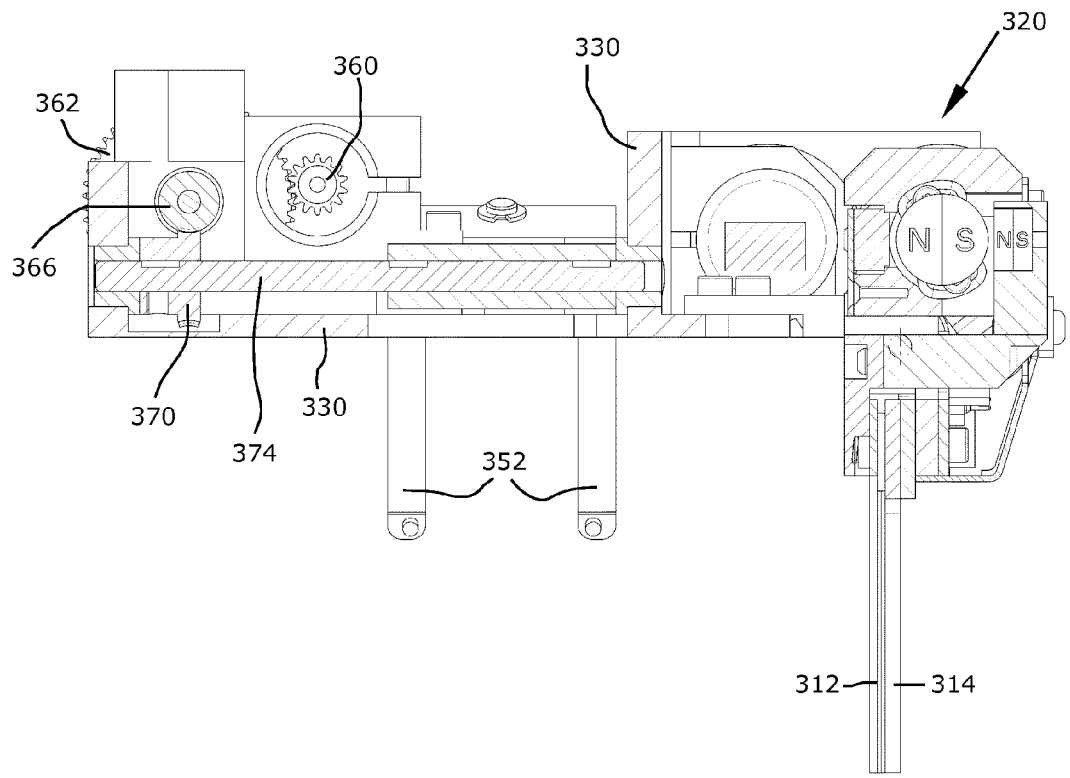
FIG. 10 is another sectional view corresponding to the section line X-X in FIG. 6.

It can also be seen from the sectional illustration in FIG. 10 that a stepping motor can be used as the gripper drive 320 for the card grippers 312, 314, said stepping motor making it possible to pivot the card grippers 312, 314 into the different positions.

The respective motors 320 and 358 for actuating the relevant grippers 312, 314 and 352, 354 are actuated by means of a control unit of the punching device, which is not illustrated in the figures. Preferably, the control is designed such that those grippers 312, 314 and 352, 354 which are currently not exerting a gripping or transporting function are pivoted into their waiting position. This can preferably be contained as a condition in the actuator, so that mutual hindrance of the grippers 312, 314 and 352, 354 can be ruled out. The control unit is also connected to further components of the punching device 10, for instance punching means 110, image capturing device 18 etc., in order likewise to be able to actuate the latter in the desired manner. Generally, the control unit is a computer having corresponding software for actuating the punching device 10 and the optional metering device 500.

The gripper unit 300 presented here affords great flexibility in use and also for handling sample cards, and also for handling receiving containers. In combination with a metering device, it is furthermore possible to feed receiving containers already filled with a liquid to the punching device in an automated manner and to feed said containers to further processing after they have been filled with punched-out sample pieces. It is conceivable for the gripper unit 300 also to be able to transport a receiving container to a further station of an overall device, for instance a station for centrifuging or a station at which the receiving containers are closed.

Of course, the gripper unit 300 presented here can also be used, irrespective of the presence of a metering device, only in the context of a punching device 10.

The invention claimed is:

1. A punching device for processing dried samples applied to a sample card comprising
    at least one punching head having a punch and a lower die, wherein the punch is movable between a rest position in which the punch is away from the lower die and a punching position in which the punch is close to the lower die, and wherein the punching head has a receiving opening into which a sample card from a sample card container is introducible by a movable gripper unit of the punching device and the movable gripper unit is positionable relative to the punching head,
    and a punching drive which is couplable or coupled to the punch of the punching head and is configured to drive the movement of the punch between the rest position and the punching position, wherein the punching device further comprises a receiving container and the punching head is configured such that a sample piece punched out of the sample card can be dispensed at an outlet opening of the lower die into a receiving recess in the receiving container arranged beneath the punching head,
    wherein the gripper unit comprises a sample card gripper and a receiving container gripper which are fitted to the gripper unit by a common frame structure and which are jointly movable by a drive unit in three main directions that are orthogonal to one another comprising a first direction, a second direction, and a third direction, the drive unit comprising a first drive, a second drive, and a third drive,
    wherein the first drive is configured to move the gripper unit in the first direction by moving the common frame structure in the first direction, and
    wherein second drive is configured to move the gripper unit in the second direction and the third drive is configured to move the gripper unit in the third direction by relative movement of the gripper unit with respect to the common frame structure.

2. The punching device as claimed in claim 1, wherein the sample card gripper and the receiving container gripper each have a gripper drive, such that associated grippers of the sample card gripper and of the receiving container gripper are movable.

3. The punching device as claimed in claim 2, wherein the movement of the receiving container gripper includes being pivotable between an open position and a closed position.

4. The punching device as claimed in claim 2, wherein the sample card gripper is pivotable about a pivot axis of the associated gripper drive, such that the sample card gripper is pivotable between a loading/unloading position facing the sample card container and a waiting position facing away from the sample card container.

5. The punching device as claimed in claim 4, wherein the sample card gripper is furthermore pivotable into a punching position located between the loading/unloading position and the waiting position, in which punching position a sample card grasped by the associated grippers is able to be fed to the punching head.

6. The punching device as claimed in claim 4, wherein the sample card gripper and the receiving container gripper are actuated by a control unit of the punching device such that when a receiving container is grasped and transported by means of the receiving container gripper the sample card gripper has been pivoted into its waiting position.

7. The punching device as claimed in claim 1, further comprising a receiving plate supporting a receiving container and having a light source illuminating at least a part of the receiving plate, wherein the light source is arranged such that at least a part of a receiving container located on the receiving plate can be illuminated from the direction of the receiving plate.

8. The punching device as claimed in claim 7, wherein the receiving recesses-provided in said receiving container can be illuminated from the direction of the receiving plate.

9. The punching device as claimed in claim 7, wherein the direction of the receiving plate is from below.

10. The punching device as claimed in claim 7, wherein at least one electroluminescent film is provided as light source on the receiving plate.

11. The punching device as claimed in claim 10, wherein the receiving plate is a transparent plate.

12. The punching device as claimed in claim 11, wherein the transparent plate is a glass plate.

13. The punching device as claimed in claim 7, wherein the electroluminescent film is arranged on the underside of the receiving plate.

14. The punching device as claimed in claim 7, further comprising a transport frame which rests on the receiving plate, is movable in the plate plane and in which at least one receiving container is receivable.

15. The punching device as claimed in claim 14, wherein the receiving plate forms a cover of a housing for a drive unit which allows the transport frame to move on the receiving plate, wherein the transport frame is coupled in a contactless manner by magnets to the drive unit covered by the receiving plate.

16. The punching device as claimed in claim 14, wherein the gripper unit is configured such that receiving containers can be moved toward and away from the transport frame by the gripper unit, wherein a receiving container in question is held by the receiving container gripper during transport.

17. The punching device as claimed in claim 1, wherein receiving containers are transportable by the gripper unit from waiting positions outside the receiving plate to processing positions on the receiving plate and vice versa.

18. The punching device as claimed in claim 1, further comprising a metering device, wherein the gripper unit is fitted on a support which is movable in one of the main directions and on which a pipetting device, which is movable in the two other main directions, of the metering device is additionally fitted, such that the gripper unit and the pipetting device are moved simultaneously in the one main direction.

19. The punching device as claimed in claim 1, wherein the dried liquid samples includes bodily fluids.

20. The punching device as claimed in claim 19, wherein the bodily fluids includes at least one of blood and saliva.

* * * * *